US007098165B2

(12) United States Patent
Weiss

(10) Patent No.: US 7,098,165 B2
(45) Date of Patent: Aug. 29, 2006

(54) MONOMETALLIC AZO COMPLEXES OF LATE TRANSITION METALS FOR THE POLYMERIZATION OF OLEFINS

(75) Inventor: Thomas Weiss, Mannheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 71 days.

(21) Appl. No.: 10/768,291

(22) Filed: Jan. 30, 2004

(65) Prior Publication Data
US 2004/0186007 A1 Sep. 23, 2004

(30) Foreign Application Priority Data
Feb. 3, 2003 (DE) ............................... 103 04 158

(51) Int. Cl.
*B01J 31/00* (2006.01)
(52) U.S. Cl. ...................... 502/150; 502/152; 502/155; 502/162
(58) Field of Classification Search ................ 502/150, 502/152, 155, 162, 167, 168; 534/692
See application file for complete search history.

(56) References Cited

U.S. PATENT DOCUMENTS

| 3,287,287 A | 11/1966 | Willis ........................ 260/2.5 |
| 5,175,326 A | 12/1992 | Klabunde .................... 556/138 |
| 6,410,664 B1 | 6/2002 | Bansleben et al. .......... 526/141 |
| 6,506,704 B1 | 1/2003 | Bansleben et al. .......... 502/155 |
| 6,506,861 B1 | 1/2003 | Wang et al. ................ 526/172 |
| 6,541,585 B1 | 4/2003 | Johnson et al. ............. 526/161 |
| 6,573,345 B1 | 6/2003 | Bansleben et al. .......... 526/161 |
| 6,576,779 B1 | 6/2003 | Bansleben et al. .......... 556/413 |
| 6,613,915 B1 | 9/2003 | Johnson et al. ............. 548/402 |
| 2002/0028741 A1 | 3/2002 | Wang et al. ................ 502/103 |
| 2002/0028897 A1 | 3/2002 | Johnson et al. ............. 526/319 |
| 2002/0032289 A1 | 3/2002 | Wang et al. ................ 526/171 |
| 2002/0037982 A1 | 3/2002 | Johnson et al. ............. 526/172 |
| 2002/0099155 A1 | 7/2002 | Inoue et al. ................ 526/172 |
| 2003/0130449 A1 | 7/2003 | Wang et al. ................ 526/134 |
| 2003/0130453 A1 | 7/2003 | Wang et al. ................ 526/172 |

FOREIGN PATENT DOCUMENTS

| DE | 199 61 340 | 7/2001 |
| WO | 02/08236 | 1/2002 |

OTHER PUBLICATIONS

Inazu et al., Some Azo-Derivatives of Tyrosol and Their Metal Complexes, Memoirs of the Faculty of Science, Kyushu University, Series C: Chemistry Bd. C5, Nr. 2, 1962, 57-63.*
Pansare et al., Azo Dyes from Cashewnut Shell Liquid Derivatives. Part II. Azo Dyes from 5-Pentadecylresorcinol, Journal of the Indian Chemical Society, Bd. 41, Nr. 4, 1964, 257-266.*
Safronova et al., Complexes of Palladiun(II) with Certain Azo Compounds and their Catalytic Properties, Journal of General Chemistry of the USSR, Bd. 54, Nr. 2, 1984, 344-346.*
Moustafa, Synthesis and Physico-Chemical Studies on Some Derivatives of o-Hydroxyphenylazo-methyl-3-Phenyl-2-Thiohydantoins and Their Chelates wirh Metal Ions, Synthesis and Reactivity in Inorganic and Metal-Organic Chemistry, Bd. 25, Nr. 6, 1995, 2883-897.*
Angew. Chem. 113, (month unavailable) 2001, pp. 550-557, Stefan Mecking, "Olefin-Polymerisation durch Komplexe später Ubergangsmetalle—ein Wegbereiter der Ziegler-Katalysatoren erscheint in neuem Gewand".
Chem. Rev., 100, (month unavailable) 2000, pp. 1169-1203, Steven D. Ittel et al, "Late-Metal Catalysts for Ethylene Homo- and Copolymerization".
Chem. Rev., 100, (month unavailable) 2000, pp. 1479-1493, Lisa S. Boffa and Bruce M. Novak, "Copolymerization of Polar Monomers with Olefins Using Transition-Metal Complexes".
Angew. Chem., 99, (month unavailable) 1987, pp. 76-77, K. Alexander Ostoja Starzewski et al, "Steuerung des Molekulargewichts von Polyethen bei der Synthese mit Bis(ylid)nickel-Katalysatoren".
J. Mol. Catal., 41, (month unavailable) 1987) pp. 123-134, Ulrich Klabunde et al, "Nickel Catalysis for Ethylene Homo- and Co-Polymerization".
Macromolecules, 35, Jul. 30, 2002, pp. 6071-6073, Dirk L. Schröder et al, "Ethylene Polymerization by Novel, Easily Accessible Catalysts Based on Nickel(II) Diazene Complexes".
Rath R K et al: "Synthesis, crystal structure and catalytic properties of (p-cymene)ruthenium (II) azophenol complexes: azophenyl to azophenol conversion by oxygen insertion to a ruthenium-carbon bond" Journal of Organometallic Chemistry, Elsevier-Sequoia S.A. Lausanne, CH, Bd. 633, Nr. 1-2, Aug. 10, 2001, Seiten 79-84, XP004318340 ISSN: 0022-328X *Verbindungen 1 bis 3 und 5 *.
Database Caplus 'Online! Chemical Abstracts Service, Columbus, Ohio, US; Aboul-Fetouh M S et al: "Physicochemical studies of some phenylhydrazone complexes" Database accession No. 2000:22764 XP002282499 *Zusammenfassung* & Al-Azhar Bulletin of Science, Bd. 9, Nr. 1, 1998, Seiten 63-70, ISSN: 1110-2535.
Sinha P K et al: "Ruthenium phenolates: synthesis, characterization and rectivities of a group of salicylaldiminato and 2-(arylazo)phenolato complexes of ruthenium" POLYHEDRON, Bd. 15, Nr. 17, 1996, Seiten 2931-2938, XP002282495 ISSN: 0277-5387 * Tabelle 1 *.
Safronova L A et al: "Complexes of palladium(II) with certain azo compounds and their catalytic properties" Journal of General Chemistry of the USSR, Bd. 54 Nr. 2, 1984, Seiten 344-346, XP009031241 ISSN: 0022-1279 *Verbindung III *.

(Continued)

Primary Examiner—Johann Richter
Assistant Examiner—Chukwuma Nwaonicha
(74) Attorney, Agent, or Firm—Jennifer R. Seng

(57) ABSTRACT

The present invention relates to compounds of transition metals with azo ligands, a process for their production, the use of these compounds as catalysts, a process for olefin (co)polymerization using these compounds, reaction products of these compounds with co-catalysts, the olefin (co) polymer, the use of these olefin (co)polymers for the production of molded parts, as well as molded parts that are produced from the olefin (co)polymers.

2 Claims, No Drawings

OTHER PUBLICATIONS

Inazu T et al: "Azo derivatives of tyrosol and their metal complexes" Memoirs of the Faculty of Science, Kyushu University, Series C: Chemistry, Bd. C5, Nr. 2, 1962, Seiten 57-63, XP009031216 ISSN: 0085-2635 * Seite 62, Zeile 7—Zeile 13 *.

Moustafa M M: "Synthesis and physico-chemical studies on some derivatives of o-hydroxy-phenylazo-1-methyl-3-phenyl-2-thiohydantoins and their chelates with metal ions" Synthesis and Ractivity in Inorganic and Metal-Organic Chemistry, Bd. 25, Nr. 6, 1995, Seiten 883-897, XP009031242 ISSN: 0094-5714 * das ganze Dokument *.

Pansare V S et al: "Azo dyes from cashew nut shell liquid derivatives. Part II. Azo dyes from 5-pentadecylresorcinol" Journal of the Indian Chemical Society, Bd. 41, Nr. 4, 1964, Seiten 257-266, XP009031226 *Verbindung IX*.

* cited by examiner

MONOMETALLIC AZO COMPLEXES OF LATE TRANSITION METALS FOR THE POLYMERIZATION OF OLEFINS

FIELD OF THE INVENTION

The present invention relates to compounds of transition metals with azo ligands, a process for their production, the use of these compounds as catalysts, a process for olefin (co)polymerization using these compounds, reaction products of these compounds with co-catalysts, the olefin (co) polymer, the use of these olefin (co)polymers for the production of molded parts, as well as molded parts that are produced from the olefin (co)polymers.

BACKGROUND OF THE INVENTION

There is a great need of catalyst compounds that are suitable for the polymerization of olefins in the presence of polar additives.

The polyolefin industry employs processes in which ethene as well as other non-polar 1-olefins are polymerized with the aid of various catalysts and free-radical initiator systems. Such polymerizations may be carried out by the use of organometallic Ziegler-Natta co-ordination catalysts, chromium catalysts and, most recently, with metallocene-like compounds of early transition metals, and also free-radical initiators. In addition it is found that these catalysts react in a very sensitive manner to a range of substances that adversely affect or completely inhibit the catalytic activity. For example, it is known that traces of oxygen, carbon monoxide, water or oxygen-containing organic compounds that act as donors can lead to a deactivation of these catalysts. If such substances are present the use of catalysts is normally restricted to free-radical initiator systems.

In order to improve this situation and also to co-polymerize polar monomers, catalysts based on late transition metals have been developed. Review articles may be found in Mecking, S. *Angew. Chem.* 2001, 113, 550; Ittel, S., Johnson, L. K. and Brookhart M. *Chem. Rev.* 2000, 100, 1169 and Boffa, L. S.; Novak, B. M. in *Chem. Rev.* 2000, 100, 1479.

The types of complexes used are typically subdivided into those with anionic ligand skeletons or those with neutral ligand skeletons. The group of complexes with an anionic ligand skeleton exhibit on account of the uncharged, (neutraly active polymerization species particularly robust properties with respect to the catalyst poisons mentioned above. The reason for this is the reduced Lewis acidity of the catalytic species. Current research is therefore concentrated specifically on such types of catalyst. Thus, Ostoja Starzewski and K. A. Witte describe in *J. Angew. Chem.* 1987, 99, 76 such catalysts with a [P,O] ligand type. Klabunde, U. and Ittel, S. D. also report on similar catalysts in *J. Mol. Catal.* 1987, 41, 123. Comparable catalysts with [P,O] complexes are also disclosed in U.S. Pat. No. 5,175,326.

A new catalyst class A conceptually similar to [P,O] complexes has also been developed, which contains an imine nitrogen donor instead of the phosphorus donor.

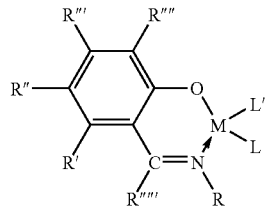

A

The common feature is large steric radicals R and R'''', which screen as far as possible the apical positions around the metal centre.

The corresponding processes for the production of such catalysts are described in more detail in WO 98/30609, WO 98/42664, WO 98/42665, DE-A 199 61 340, WO 00/56785, WO 01/92347 and WO 02/08236.

It was now surprisingly found that special azo dyes can also be incorporated into a number of anionic ligand systems for purposes of complexing. Azo dyes represent a class of compounds that has already been investigated in detail, and which in addition can be synthesized on an industrial scale.

Such ligands for the production of single-site catalysts for the polymerization of olefins are disclosed by Schroder, D. L., Keim, W., Zuideveld, M. A., Mecking, S. in *Macromolecules*, 2002, 35, 6071. Activation with widely different Lewis acids in the presence of polar additives as well as sterically demanding ortho-substituted compounds that have a specific influence on the activity and molecular weight are not disclosed however.

In EP-A 1 170 308 ligands are described that likewise exhibit an azo finction but, in contrast to the claimed complexes, do not have an oxygen-metal bond but instead have an amide-type nitrogen-metal bond. Also, no transition metal compounds with late transition elements are disclosed. No sterically demanding substituents in the ortho position to the amide-type nitrogen in such complexes are described.

DE-A 123747 disclosed a monometallic, chelating azo ligand that has, in addition to the azo donor function, a metal-carbon(phenyl) bond, i.e. not an oxygen-metal bond but a carbanionic phenyl-metal bond. Since metal-phenyl bonds of nickel have been shown to be polymerization active, the complex postulated in DE-A 123747 would not co-ordinate the metal centre in a chelate-type manner during the polymerization. The disadvantage with this process is therefore the change in the geometry of the metal complex during the polymerization. Accordingly good results are not expected as regards the uniformity of the polymers.

SUMMARY OF THE INVENTION

The present invention is directed to compounds that permit an olefin (co)polymerization in the presence of polar additives.

The present invention is directed to compounds of the general formula (I)

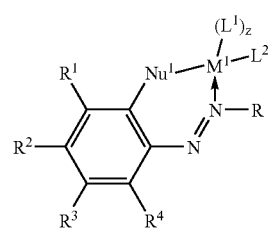

wherein

Nu$^1$ denotes —O, —S, —Se, —PR$^a$, NR$^a$ or —COO groups,

R$^a$ denotes hydrogen, alkyl or aryl radicals and

R, R$^1$, R$^2$, R$^3$ and R$^4$ are identical or different radicals that are selected independently of one another from the group of H, halogens, substituted or unsubstituted C$_1$–C$_8$-alkyl, C$_2$–C$_8$-alkenyl, C$_3$–C$_{12}$-cycloalkyl, C$_7$–C$_{13}$-aralkyl and C$_6$–C$_{14}$-aryl groups, and R$^1$ with R$^2$, R$^3$ or R$^4$, and R$^2$ with R$^3$ or R$^4$ may form a ring, $M^1$ denotes an element of the 4$^{th}$ to 12$^{th}$ subgroup of the Periodic System,
$L^1$ is a neutral ligand and
$L^2$ is an anionic ligand, wherein $L^1$ and $L^2$ may be coupled together by one or more covalent bonds, and
z is a whole number from 1 to 3.

DETAILED DESCRIPTION OF THE INVENTION

Preferably, compounds in which
$Nu^1$ is O,
R is selected from the group of substituted or unsubstituted $C_6$–$C_{14}$-aralkyl groups,
$R^1$, $R^2$, $R^3$ and $R^4$ are identical or different radicals and are selected independently of one another from the group of H, substituted or unsubstituted $C_1$–$C_8$-alkyl groups, $C_2$–$C_8$-alkenyl groups, $C_3$–$C_{12}$-cycloalkyl groups, $C_7$–$C_{13}$-aralkyl groups and $C_6$–$C_{14}$-aryl groups,
$M^1$ is selected from the group of Ti, Zr, Hf, Cr, V, Fe, Co, Ni, Ru, Rh, Pd, Os, Ir, Pt, Cu, Ag, Au, Zn, Cd and Hg
$L^1$ is an organic or inorganic neutral ligand selected from the group of phosphanes of the general formula $(R^{13})_xPH_{3-x}$, amines of the general formula $(R^{13})_xNH_{3-x}$, ethers of the general formula $(R^{13})_2O$, alcohols of the general formula $(R^{13})OH$, pyridine derivatives of the general formula $C_5H_{5-x}(R^{13})_xN$, CO, $C_1$–$C_{12}$-alkyl nitriles, $C_6$–$C_{14}$-aryl nitriles, and singly or multiply ethylenically unsaturated double bond systems, wherein
$R^{13}$ is selected from the group of H, $C_1$–$C_8$-alkyl groups, benzyl radicals and $C_6$–$C_{14}$-aryl groups and
x is a whole number from 0 to 3 and
$L^2$ is an anionic ligand selected from the group of halide ions, amide anions of the formula $R^{14}R^{15}N$, $C_1$–$C_6$-alkyl anions, allyl anions, methallyl anions, benzyl anions and aryl anions, wherein
$R^{14}$ and $R^{15}$ independently of one another are selected from the group of H, $C_1$–$C_8$-alkyl groups, benzyl radicals and $C_6$–$C_{14}$-aryl groups, and $R^{14}$ may also be covalently coupled to $R^{15}$, and
z may be a whole number from 1 to 3.
More preferably are compounds in which
$Nu^1$ is O,
R is mesityl, 2,4,6-trimethylphenyl or 2,6-diisopropylphenyl,
$R^1$, $R^2$, $R^3$ and $R^4$ are identical or different radicals and independently of one another are selected from the group of H, $C_1$–$C_8$-alkyl groups and $C_6$–$C_{14}$-aryl groups,
$M^1$ is selected from the group of Ti, Zr, Cr, V, Fe, Co, Ni, Pd, Cu and Zn
$L^1$ is a neutral ligand selected from the group of triphenylphosphine, triethylphosphine, trimethylphosphine, dibenzophosphol, triphenyl phosphite, triethyl phosphite, trimethyl phosphite, triphenyl phosphite, trimethylamine, triethylamine, dimethylaniline, diethylaniline, benzyldimethylamine, benzyldiethylamine, diisopropylamine, diethylamine, dimethylamine, diphenylamine, diethyl ether, tetrahydrofuran, water, methanol, ethanol, pyridine, 2-picoline, 3-picoline, 4-picoline, 2,3-lutidine, 2,4-lutidine, 2,5-lutidine, 2,6-lutidine, 3,5-lutidine, CO, acrylonitrile, acetonitrile, propionitrile, butyronitrile, benzonitrile, ethenyl, propenyl, cis-2-butenyl, trans-2-butenyl, cyclohexenyl and norbornenyl,
$L^2$ is an anionic ligand selected from the group of chloride, bromide, dimethylamide, diethylamide, amide, allyl, methyl, ethyl, n-propyl, i-propyl, n-butyl, tert.-butyl, hexyl and phenyl z may be a whole number from 1 to 3.
More preferably compounds according to the present invention include those in which
$Nu^1$ is O,
R is mesityl or 2,6-diisopropylphenyl,
$R^1$ is tert.-butyl or phenyl,
$R^2$ is H,
$R^3$ is tert.-butyl,
$R^4$ is H,
$M^1$ is Ni or Pd,
$L^1$ is triphenylphosphane or pyridine,
$L^2$ is phenyl or methyl and
z is a whole number from 1 to 3.

The present invention also provides a process for the production of the compounds according to the present invention, in which a ligand of the general formula II

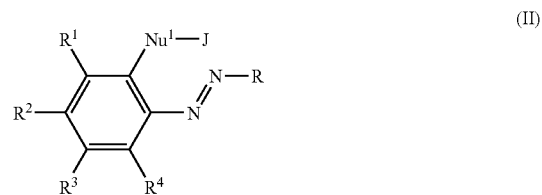

where
J is selected from the group of H and an element of the 1$^{st}$ or 2$^{nd}$ main group of the Periodic System and wherein $Nu^1$, R, $R^1$, $R^2$, $R^3$, $R^4$ have the same meanings as above, is reacted with 0.2 to 5 equivalents of a metal compound of the general formulae $M^1X_4$, $M^1X_3$, $M^1L^1L^2$, or $M^1X_2$, in which
$M^1$, $L^1$ and $L^2$ have the same meanings as above and
X is selected from the group of halogen, $C_1$–$C_8$-alkyl, $C_3$–$C_{12}$-cycloalkyl, $C_7$–$C_{13}$-aralkyl and $C_6$–$C_{14}$-aryl groups and in which $M^1X_4$, $M^1X_3$ or $M^1X_2$ may be stabilized by further neutral ligands.

The process for the production of the compounds according to the present invention can be carried out so that the compounds can be purified by crystallization and isolated after reaction of the ligand with the metal compounds.

The process for the production of the compounds according to the present invention can be carried out so that the ligand and the metal compound are reacted in situ in the presence of one or more olefinic monomers. The process for the production of the compounds according to the present invention can be carried out in aprotic polar solvents.

The present invention furthermore provides for the use of the compounds according to the present invention as catalysts.

The compounds according to the present invention can be used as polymerization catalysts.

The present invention also provides a process for the production of olefin (co)polymers in which the compounds according to the present invention are reacted in the presence of olefinic monomers selected from the group of 1-olefins, cycloolefins, functionalized 1-olefins and mixtures thereof.

This process can be carried out in the presence of boron or aluminum compounds as co-catalysts.

The molar ratio of co-catalyst to metal M¹ in the compound according to the present invention can be in the range from 1:10 to 1:10000 for the polymerization process.

Aluminoxanes can be used as co-catalysts in the polymerization process.

The polymerization process can be carried out in polar solvents or solvent mixtures.

The present invention further provides reaction products that are formed by reacting the compounds according to the present invention with the co-catalysts.

The present invention also provides the olefin (co)polymer that is produced by the polymerization in the presence of the compounds according to the present invention.

The present invention further provides for the use of the olefinic (co)polymer for the production of all types of molded parts.

The present invention also provides molded parts that may be obtained by processing the olefin (co)polymer.

In the compounds of the general formula (I)

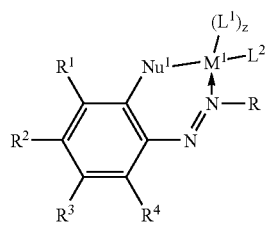

(I)

Nu¹ is selected from the group of —O, —S, —Se, —PR$^a$, —NR$^a$ or —COO groups, wherein R$^a$ denotes hydrogen, alkyl or aryl radicals. O, NR$^a$ and COO groups are preferably used for Nu¹. Nu¹ more preferably denotes oxygen.

R, R¹, R², R³ and R⁴ are in this connection identical or different radicals that are selected independently of one another from the group of H, halogens, substituted or unsubstituted $C_1$–$C_8$-alkyl, substituted or unsubstituted $C_2$–$C_8$-alkenyl, substituted or unsubstituted $C_3$–$C_{12}$-cycloalkyl, substituted or unsubstituted $C_7$–$C_{13}$-aralkyl and substituted or unsubstituted $C_6$–$C_{14}$-aryl groups, substituted or unsubstituted nitro groups, and R¹ may together with R², R³ or R⁴ form a ring, and R² may together with R³ or R⁴ form a ring, R, R¹, R², R³ and R⁴ may be all halogens such as fluorine, chlorine, bromine and iodine. Fluorine and chlorine are preferred.

R, R¹, R², R³ and R⁴ may be all substituted or unsubstituted alkyl radicals that in the main chain contain the number of carbon atoms mentioned above. Preferred unsubstituted alkyl radicals include methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, iso-heptyl and n-octyl. More preferred are $C_1$–$C_6$-alkyl groups such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl and sec.-hexyl. Most preferred are $C_1$–$C_4$-alkyl groups such as methyl, ethyl, n-propyl, iso-propyl, n-butyl, iso-butyl, sec.-butyl and tert.-butyl, wherein these groups may in each case carry one or more further substituents. Preferred further substituents are all halogen atoms, particularly preferred being fluorine, chlorine and bromine. More preferred are fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl. Most preferred are fluoromethyl, difluoromethyl, trifluoromethyl and perfluorobutyl.

R, R¹, R², R³ and R⁴ may be all substituted or unsubstituted alkenyl radicals that in the main chain contain the number of carbon atoms mentioned above. Preferred unsubstituted alkenyl groups are alkenyl groups with 1 to 4 isolated or conjugated double bonds. More preferred are vinyl, 1-allyl, 3-allyl, ω-butenyl, ω-pentenyl, ω-hexenyl, 1-cis-buta-1,3-dienyl and 1-cis-hexa-1,5-dienyl, wherein these groups may in each case also carry further substituents. Preferred substituted alkenyl groups include isopropenyl, 1-isopropenyl, α-styryl, β-styryl, 1-cis-1,2-phenylethenyl and 1-trans-1,2-phenylethenyl.

R, R¹, R², R³ and R⁴ may be all substituted or unsubstituted cycloalkyl radicals that contain the aforementioned number of carbon atoms in the ring. Preferred unsubstituted cycloalkyls include cyclopropyl, cyclobutyl, cyclopentyl, cyclohexyl, cycloheptyl, cyclooctyl, cyclononyl, cyclodecyl, cycloundecyl and cyclododecyl. More preferred are cyclopentyl, cyclohexyl and cycloheptyl. The cycloalkyls may also carry further substituents. Preferred substituted cycloalkyl groups are 2-methylcyclopentyl, 3-methylcyclopentyl, cis-2,4-dimethylcyclo-pentyl, trans-2,4-dimethylcyclopentyl, cis-2,5-dimethyl-cyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethyl-cyclohexyl, trans-2,6-dimethylcyclohexyl, cis-2,6-diisopropylcyclohexyl, trans-2,6-diisopropylcyclohexyl, 2,2,6,6-tetramethyl-cyclohexyl, 2-methoxycyclo-pentyl, 2-methoxycyclohexyl, 3-methoxycyclopentyl, 3-methoxycyclohexyl, 2-chlorocyclopentyl, 3-chlorocyclopentyl, 2,4-dichloro-cyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl and 3-thiomethylcyclohexyl.

R, R¹, R², R³ and R⁴ may be all substituted or unsubstituted aralkyl radicals that contain the aforementioned number of carbon atoms along the main chain. Preferred unsubstituted aralkyl radicals are $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenyl-ethyl), 1-phenylbutyl, 2-phenylbutyl, 3-phenylbutyl and 4-phenylbutyl. Benzyl is more preferred. The substituents for the aralkyl radicals are alkyl, aryl, aralkyl, alkoxy, aryloxy, aralkyloxy, dialkylamino, halogen, keto and hydroxyl.

R, R¹, R², R³ and R⁴ may be all substituted or unsubstituted aryl groups that contain the aforementioned number of carbon atoms in the ring. Preferred unsubstituted aryl radicals are phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl. More preferred are phenyl, 1-naphthyl and 2-naphthyl. Phenyl is most preferred. These aryl groups may carry further substituents. Among the substituted alkyl, alkenyl, cycloalkyl, aralkyl and aryl groups there may be mentioned not only the already preferred substituents, but also:

Substituted and/or unsubstituted $C_1$–$C_8$-alkyl groups such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, isoheptyl and n-octyl. Preferred are $C_1$–$C_6$-alkyl, more preferred are $C_1$–$C_4$-alkyl such as methyl, ethyl, n-propyl, iso-propyl, n-butyl, iso-butyl, sec.-butyl and tert.-butyl. Substituted $C_1$–$C_8$-alkyl groups are understood to include singly or multiply halogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl. Preferred are fluoromethyl, difluoromethyl, trifluoromethyl and perfluorobutyl.

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl. Preferred are cyclopentyl, cyclohexyl and cycloheptyl.

$C_7$–$C_{13}$-aralkyl, preferred being $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl. Benzyl is more preferred.

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl. Preferred are phenyl, 1-naphthyl and 2-naphthyl. More preferred is phenyl.

One or more halogens independently selected from one another such as fluorine, chlorine, bromine or iodine. Fluorine and/or chlorine are more preferred.

Nitro and/or nitroso groups. Nitro is more preferred.

$C_1$–$C_6$-alkoxy groups such as methoxy, ethoxy, n-propoxy, iso-propoxy, n-butoxy, iso-butoxy, sec.-butoxy, tert.-butoxy, n-pentoxy, iso-pentoxy, n-hexoxy and iso-hexoxy. Preferred are methoxy, ethoxy, n-propoxy and n-butoxy.

$C_6$–$C_{14}$-aryloxy groups such as phenoxy, ortho-cresyloxy, meta-cresyloxy, para-cresyloxy, α-naphthoxy, β-naphthoxy or 9-anthryloxy.

Silyl groups of the general formula $SiR^{10}R^{11}R^{12}$, wherein $R^{10}$, $R^{11}$ and $R^{12}$ independently of one another are selected from the group of hydrogen, $C_1$–$C_9$-alkyl groups, benzyl radicals and $C_6$–$C_{14}$-aryl groups. Preferred are the trimethylsilyl, triethylsilyl, triisopropylsilyl, diethylisopropylsilyl, dimethylhexylsilyl, tert.-butyldimethylsilyl, tert.-butyldiphenylsilyl, tribenzylsilyl, triphenylsilyl and the tri-para-xylylsilyl group. More preferred are the trimethylsilyl group and the tert.-butyldimethylsilyl group.

Silyloxy groups $OSiR^{10}R^{11}R^{12}$, where $R^{10}$, $R^{11}$ and $R^{12}$ independently of one another are selected from the group of hydrogen, $C_1$–$C_8$-alkyl groups, benzyl radicals and $C_6$–$C_{14}$-aryl groups. Preferred are the trimethylsilyloxy, triethylsilyloxy, triisopropylsilyloxy, diethylisopropylsilyloxy, dimethylhexylsilyloxy, tert.-butyldimethylsilyloxy, tert.-butyldiphenylsilyloxy, tribenzylsilyloxy, triphenylsilyloxy and the tri-para-xylylsilyloxy group. More preferred are the trimethylsilyloxy group and the tert.-butyldimethylsilyloxy group.

Five-membered or six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl. These five-membered and six-membered nitrogen-containing heteroaryl radicals may now contain further substituents such as $C_1$–$C_8$-alkyl groups. Preferred in this case are methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, isoheptyl and n-octyl. More preferred are $C_1$–$C_6$-alkyl groups. Most preferred are $C_1$–$C_4$-alkyl groups such as methyl, ethyl, n-propyl, iso-propyl, n-butyl, iso-butyl, sec.-butyl and tert.-butyl. These $C_1$–$C_8$-alkyl groups may also carry further substituents on the heteroaryl radicals. Such further substituents include:

Halogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl.

Preferred are fluoromethyl, difluoromethyl, trifluoromethyl and perfluorobutyl.

$C_3$–$C_{12}$-cycloalkyls such as cyclopropyl, cyclobutyl, cyclopentyl, cyclohexyl, cycloheptyl, cyclooctyl, cyclononyl, cyclodecyl, cycloundecyl and cyclododecyl. Preferred are cyclopentyl, cyclohexyl and cycloheptyl.

$C_7$–$C_{13}$-aralkyls. Preferred are $C_7$–$C_{12}$ phenylalkyls such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl. Benzyl is more preferred.

$C_6$–$C_{14}$-aryls. Preferred are phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl. More preferred are phenyl, 1-naphthyl and 2-naphthyl. Most preferred is phenyl.

Halogens such as fluorine, chlorine, bromine or iodine. Preferred are fluorine or chlorine.

$C_1$–$C_6$-alkoxy groups such as methoxy, ethoxy, n-propoxy, iso-propoxy, n-butoxy, iso-butoxy, sec.-butoxy, tert.-butoxy, n-pentoxy, iso-pentoxy, n-hexoxy and iso-hexoxy. Preferred are methoxy, ethoxy, n-propoxy and n-butoxy.

$C_6$–$C_{14}$-aryloxy groups such as phenoxy, ortho-cresyloxy, meta-cresyloxy, para-cresyloxy, α-naphthoxy, β-naphthoxy or 9-anthryloxy.

Silyl groups $SiR^{10}R^{11}R^{12}$, where $R^{10}$, $R^{11}$ and $R^{12}$ independently of one another are selected from the group of hydrogen, $C_1$–$C_8$-alkyl groups, benzyl radicals and $C_6$–$C_{14}$-aryl groups. Preferred are the trimethylsilyl, triethylsilyl, triisopropylsilyl, diethylisopropylsilyl, dimethylhexylsilyl, tert.-butyldimethylsilyl, tert.-butyldiphenylsilyl, tribenzylsilyl, triphenylsilyl and the tri-para-xylylsilyl group. Preferred are the trimethylsilyl group and the tert.-butyldimethylsilyl group.

Silyloxy groups $OSiR^{10}R^{11}R^{12}$, where $R^{10}$, $R^{11}$ and $R^{12}$ independently of one another are selected from the group of hydrogen, $C_1$–$C_8$-alkyl groups, benzyl radicals and $C_6$–$C_{14}$-aryl groups. Preferred are the trimethylsilyloxy, triethylsilyloxy, triisopropylsilyloxy, diethylisopropylsilyloxy, dimethylhexylsilyloxy, tert.-butyldimethylsilyloxy, tert.-butyldiphenylsilyloxy, tribenzylsilyloxy, triphenylsilyloxy and the tri-para-xylylsilyloxy group. Preferred are the trimethylsilyloxy group and the tert.-butyldimethylsilyloxy group.

Preferably, the radical R is selected from the group of mesityl, 2,4,6-trimethyl-phenyl or 2,6-diisopropylphenyl. More preferably R is mesityl or 2,6-diisopropylphenyl. The radicals $R^1$ and $R^3$ are preferably selected from the group of H, $C_1$–$C_8$-alkylene, $C_6$–$C_{14}$-arylene, substituted or unsubstituted nitro groups, fluorine and chlorine. Preferably $R^1$ and $R^3$ are selected from the group of tert.-butyl and phenyl. $R^2$ and $R^4$ are preferably hydrogen.

According to the present invention the radicals $R^1$ to $R^4$ may be joined together to form a five-membered to twelve-membered ring. Thus, the following may be introduced at the positions of $R^1$ and $R^2$, $R^1$ and $R^3$, $R^1$ and $R^4$, $R^2$ and $R^3$, $R^2$ and $R^4$ as well as $R^3$ and $R^4$ —$(CH_2)_3$-(trimethylene), —$(CH_2)_4$-(tetramethylene), —$(CH_2)_5$-(pentamethylene), —$(CH_2)_6$-(hexa-methylene), —$CH_2$—CH=CH—, —$CH_2$—CH=CH—$CH_2$—, —CH=CH—CH=CH—, —O—$CH_2$—O—, —O—CHMe—O—, —O—CH—$(C_6H_5)$—O—, —O—$CH_2$—$CH_2$—O—, —O—$CHMe_2$-O—, —NMe-$CH_2$—$CH_2$—NMe-, —NMe-$CH_2$—NMe- or —$OSiME_2$-O— where Me=$CH_3$ bridges.

The central atom of the compound (I) $M^1$ is preferably selected from the group of elements of the $4^{th}$ to $12^{th}$ subgroups of the Periodic System. Preferred are the elements Ti, Zr, Hf, Cr, V, Fe, Co, Ni, Ru, Rh, Pd, Os, Ir, Pt, Cu, Ag, Au, Zn, Cd and Hg. More preferred are Ti, Zr, Cr, V, Fe, Co, Ni, Pd, Cu and Zn. Most preferred are Ni and Pd.

The radical $L^1$ is a neutral ligand. Among neutral ligands there may be mentioned all neutral ligands known to the person skilled in the art. Preferred are organic or inorganic neutral ligands selected from the group comprising phosphanes of the general formula $(R^{13})_x PH_{3-x}$, amines of the general formula $(R^{13})_x NH_{3-x}$, ethers of the general formula $(R^{13})_2 O$, alcohols of the general formula $(R^{13})OH$, pyridine derivatives of the general formula $C_5H_{5-x}(R^{13})_x N$, CO, $C_1$–$C_{12}$-alkyl nitriles, $C_6$–$C_{14}$-aryl nitriles and singly or multiply ethylenically unsaturated double bond systems.

The radical $R^{13}$ in the general formula of the phosphanes, amines, ethers, alcohols and pyridine derivatives is selected from the group of H, $C_1$–$C_8$-alkyl groups, the benzyl group and $C_6$–$C_{14}$-aryl groups. The definition of $C_1$–$C_8$-alkyl groups and $C_6$–$C_{14}$-aryl groups is understood to include all substituted and unsubstituted alkyl and aryl groups as well as their preferred ranges that have already been defined for the radicals R, R, $R^1$, $R^2$, $R^3$ and $R^4$ in the respective range of number of carbon atoms. The index x denotes a whole number from 0 to 3. For phosphanes and amines x is preferably 3, and for pyridine derivatives x is preferably 0 or 1.

Preferred phosphanes for the radical $L^1$ are triphenylphosphane, perfluorotriphenylphosphane, trimethylphosphane, triethylphosphane, dibenzo-phosphol and tricyclohexylphosphane. Preferred amines are trimethylamine, triethylamine, dimethylbenzylamine. Preferred ethers are diethyl ether, tetrahydrofuran and water. Preferred alcohols are methanol, ethanol, isopropanol. Preferred pyridine derivatives are pyridine, 2-picoline, 3-picoline, 4-picoline, 2,3-lutidine, 2,5-lutidine, 2,6-lutidine, 3,5-lutidine. Preferred alkyl nitriles are acetonitrile, propionitrile as well as butyronitrile, malonic acid nitrile, oxalic acid nitrile, succinic acid nitrile, acrylic acid nitrile, fumaric acid nitrile and maleic acid nitrile. Preferred aryl nitriles are benzonitrile, 2-naphthyl nitrile, 1-naphthyl nitrile and terephthalic acid nitrile. Preferred ethylenically unsaturated double bond systems are ethenyl, propenyl, cis-2-butenyl, trans-2-butenyl, cyclohexenyl and norbornenyl.

Triphenylphosphane and pyridine are more preferred as $L^1$.

The radical $L^2$ is an anionic ligand that may optionally be coupled to $L^1$ by one or more covalent bonds. An anionic ligand is understood to be any anionic ligand known to the person skilled in the art. Preferred are anionic ligands selected from the group of halide ions, amide anions of the general formula $R^{14}R^{15}N$, $C_1$–$C_6$-alkyl anions, allyl anions, methallyl anions, benzyl anions and aryl anions.

The radicals $R^{14}$ and $R^{15}$ are in this connection selected independently of one another from the group of H, $C_1$–$C_8$-alkyl groups, a benzyl group and $C_6$–$C_{14}$-aryl groups, wherein $R^{14}$ and $R^{15}$ may also be covalently coupled. The definition of the $C_1$–$C_8$-alkyl groups and $C_6$–$C_{14}$-aryl groups is understood to include all substituted and/or unsubstituted alkyl groups and aryl groups as well as their preferred ranges that have already been defined for the radicals R, $R^1$, $R^2$, $R^3$ and $R^4$ in the respective range of number of carbon atoms.

Preferred halide ions for the radical $L^2$ are chloride and bromide. Preferred amide anions are amide, dimethylamide, diethylamide, diisopropylamide, diphenylamide, anilide, methylphenylamide. Preferred alkyl anions are methyl, ethyl, n-propyl, i-propyl, n-butyl, tert.-butyl and hexyl. Preferred allyl anions are 1,3-aryl-substituted allyl anions, 1,3-bistrimethylsilyl-substituted allyl anions, preferably the parent compound $C_3H_5^-$. Anions of methacrylic acid esters, 2-aryl-substituted methallyl anions and the parent compound $C_4H_8^-$ are the preferred methallyl anions. The benzyl anion is furthermore preferred. Phenyl is the preferred aryl anion.

Z is a whole number in the range from 1 to 3, preferably in the range from 1 to 2.

In order to obtain the compounds according to the present invention, ligands of the formula (II)

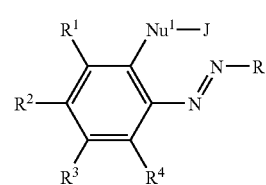

(II)

are reacted with metal compounds of the general formulae $M^1X_4$, $M^1X_3$, $M^1L^1L^2$, or $M^1X_2$.

Preferred metal compounds of the general formula $M^1L^1L^2$ are those in which the radicals $L^1$ and $L^2$ are coupled to one another by means of a covalent bond. Preferred are 1,5-cyclooctadienyl ligands ("COD"), 1,6-cyclodecenyl ligands or 1,5,9-all-trans-cyclododecatrienyl ligands.

According to the present invention $L^1$ can be tetramethylethylenediamine, in which only one nitrogen is co-ordinated to $M^1$.

The radical J denotes in this connection H or an element from the $1^{st}$ or $2^{nd}$ main groups of the Periodic System. J is preferably H, Na, Li, Mg, Ca.

The radical X is selected from the group of halogens, $C_1$–$C_8$-alkyl groups, $C_3$–$C_{12}$-cycloalkyl groups, $C_7$–$C_{13}$-aralkyl groups and $C_6$–$C_{14}$-aryl groups.

Among the halogens, chlorine and bromine are preferred.

$C_1$–$C_8$-alkyl groups are understood to denote all substituted or unsubstituted alkyl groups with this number of carbon atoms. Preferred are methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, iso-heptyl and n-octyl; more preferred are $C_1$–$C_6$-alkyl such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl and sec.-hexyl. Most preferred are $C_1$–$C_4$-alkyl such as methyl, ethyl, n-propyl, iso-propyl, n-butyl, iso-butyl, sec.-butyl and tert.-butyl.

$C_3$–$C_{12}$-cycloalkyl groups are understood to denote all substituted or unsubstituted cycloalkyl groups with this number of carbon atoms in the ring. Preferred are cyclopropyl, cyclobutyl, cyclopentyl, cyclohexyl, cycloheptyl, cyclooctyl, cyclononyl, cyclodecyl, cycloundecyl and cyclododecyl. More preferred are cyclopentyl, cyclohexyl and cycloheptyl.

$C_7$–$C_{13}$-aralkyl groups are understood to denote all substituted or unsubstituted aralkyl groups with this number of carbon atoms. Preferred are $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenyl-ethyl), 1-phenylbutyl, 2-phenylbutyl, 3-phenylbutyl and 4-phenylbutyl. Benzyl is more preferred.

$C_6$–$C_{14}$-aryl groups are understood to denote all substituted or unsubstituted aryl groups with this number of carbon atoms in the ring. Preferred are phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, more preferred are phenyl, 1-naphthyl and 2-naphthyl, and most preferred is phenyl.

In this connection $M^1X_2$, $M^1X_3$, $M^1X_4$ may optionally be stabilized by neutral ligands. Neutral ligands are understood to denote all ligands in the chemistry of complexes known to the person skilled in the art. Preferred are cyclic and non-cyclic ethers, amines, diamines, nitriles, isonitriles or phosphines, and unsaturated cycloaliphatic compounds. More preferred are diethyl ether, tetrahydrofuran, 1,2-dimethoxyethane, tetramethylethylenediamine, acetonitrile, triphenylphosphane or cyclooctadienes.

It is preferred to use these neutral ligands if Ni-dialkyl compounds are to be employed as metal compounds of the type $M^1X_2$. The neutral ligands may also be used as solvents.

The compounds of the formula (I) may either be produced or isolated in situ by reacting the ligands of the formula (II) with the metal compounds of the formulae $M^1X_4$, $M^1X_3$, $M^1L^1L^2$ or $M^1X_2$, or alternatively may be formed by reaction in the presence of olefinic monomers.

The production of the compounds according to the present invention of the general formula (I) is generally carried out using ligands of the general formula (II) in which the radicals are as defined above. In order to synthesize the compounds according to the present invention the ligands may either be freed from the radical J with the aid of a base and then reacted with metal compounds of the general formulae $M^1X_2$, $M^1X_3$, $M^1X_4$ or $M^1(O)$ complexes such as $M^1L^1L^2$, or alternatively may be reacted directly with the metal compounds without using a base.

The metal alkyls known to the person skilled in the art may be used as base. Preferred are methyllithium, ethyl-lithium, n-butyllithium, sec.-butyllithium, tert.-butyllithium, hexyllithium, Grignard compounds such as ethylmagnesium bromide, and furthermore lithium amide, sodium amide, potassium amide, potassium hydride or lithium diisopropylamide ("LDA"). As solvents high boiling point solvents such as toluene, ortho-xylene, meta-xylene, para-xylene, ethylbenzene or mixtures thereof have proved preferably suitable as solvents, though non-cyclic or cyclic ethers such as 1,2-dimethoxyethane, tetrahydrofuran or diethyl ether may also be used.

This removal of the radical J is complete in a time ranging from 1 minute to 12 hours. A reaction duration of 2 to 10 hours is preferred, 3 to 5 hours being more preferred. During the reaction the temperature is in the range from –196° to 0° C. A temperature in the range from –90° to –20° C. is preferred.

For the reaction of the ligand with the base there may be used all aprotic, polar or non-polar solvents known to the person skilled in the art. Aprotic, polar solvents are preferred, such as methylene chloride, acetonitrile, acrylonitrile, benzonitrile, tetrahydrofuran, diethyl ether or lutidine.

After the reaction with the base the solvent is removed from the product in a manner known to the person skilled in the art. The metallated ligand that is obtained may be purified in a manner known to the person skilled in the art. The preferred purification method is crystallization.

In the reaction of the metallated or non-metallated ligand of the formula (II) with the metal compounds of the formulae $M^1X_2$, $M^1X_3$, $M^1X_4$ and $M^1L^1L^2$, the solvents known to the person skilled in the art are used. Preferred solvents include benzene, toluene, ethylbenzene, ortho-xylene, meta-xylene or para-xylene, chlorobenzene, cyclohexane, acetonitrile, tetrahydrofuran, methylene chloride or mixtures thereof. The reaction is carried out in the temperature range known to the person skilled in the art. The reaction is preferably carried out in a temperature range from –100° C. to +150° C., more preferably in the range from –78° C. to +100° C. The reaction of the ligands with the metal compounds, as also the reaction of the ligands with the bases, must take place under the exclusion of oxygen and moisture.

The molar ratios of ligand to $M^1$ are in the range from 5:1 to 1:5. Amounts in the range from 1:1 to 1:3 are preferred, stoichiometric amounts being more preferred.

The purification of the compounds according to the present invention of the general formula (I) is carried out according to methods known to the person skilled in the art, such as crystallization, filtration through Celite® and chromatography. Crystallization is preferred.

For the polymerization it is not necessary to isolate the compounds according to the present invention. A ligand of the general formula (II) may also be reacted with a suitable metal compound of the formula $M^1X_2$, $M^1X_3$, $M^1X_4$, or $M^1(O)$ complexes such as $M^1L^1L^2$ only immediately before the polymerization and produced in situ.

If X in the metal compound of the formula $M^1X_2$, $M^1X_3$ or $M^1X_4$ or $L^2$ in $M^1L^1L^2$ is selected from the group of $C_1$–$C_6$-alkyl groups, benzyl anions or aryl anions, then the deprotonation of the ligand of the general formula (II) may be omitted. In these cases it has proved preferable not to isolate the complex compounds according to the present invention but to produce them in situ only immediately before the polymerization.

The production of the ligands of the general formula (II) is carried out by reacting aromatic compounds of the general formula (III)

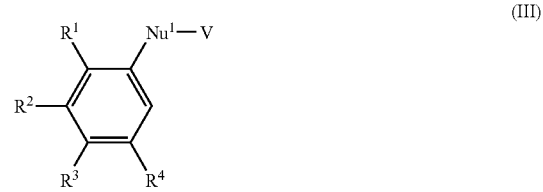

(III)

where V may be hydrogen, Li, Na, K, Mg, Ca and Sr, with electrophilic aryl diazonium salts of the general formula (IV)

$$R\!-\!N_2^+A^- \qquad\qquad (IV)$$

in which the radicals $Nu^1$, R, $R^1$, $R^2$, $R^3$, $R^4$ are as defined above and $A^-$ denotes an anion of strong acids selected from the group of $F^-$, $Cl^-$, $Br^-$, $I^-$, $SO_4^{2-}$, $NO_3^-$, $ClO_4^-$, $ClO_3^-$, $CF_3OO^-$, $CF_3SO_3^-$, $BF_4^-$, $PF_6^-$, $B(C_6F_5)_4^-$ and anionic metallate complexes.

The preparation of the alkali metal or alkaline earth metal compounds of the general formula (III) is then carried out following the diazotisation at temperatures of −78° C. to +150° C., preferably at −20° C. to +75° C. Diethyl ether or tetrahydrofuran are preferably used. Other conventional solvents such as toluene, hexane, acetonitrile may however also be used.

The preparation of diazonium salts is described by a) Zollinger, H. in Chemie der Azofarbstoffe, 1958, Birckhäuser Verlag, b) by Hashida, Y., Landells, R. G. M., Lewis, G. E., Szele, I., Zollinger, H. in *J. Am. Chem. Soc.* 1978, 100, 2816, c) by Laali, K., Szele, I., Zollinger, H. in *Helv. Chim. Acta* 1983, 66, 1737 and d) in Houben-Weyl, Methoden der Organischen Chemie, Vol. X/3 p. 220 and is generally known to the person skilled in the art.

In the diazotisation aromatic amines are reacted in the presence of Lewis or Brönsted acids and nitrosating agents such as organic or inorganic nitrites. $BF_3$ is suitable as Lewis acid, and $HBF_4$, sulfuric acid, HCl or HF are suitable as Brönsted acids. The reaction takes 1 to 48 hours, preferably 1 to 15 hours. Preferred solvents for inorganic nitrites include strong acids and also protic polar solvents such as water, methanol or mixtures thereof. On the other hand when using organic nitrites such as iso-amyl nitrite, it is preferred to use aprotic polar solvents such as tetrahydrofuran or esters, and preferably methylene chloride. In this connection the diazonium salts can be isolated as sparingly soluble solids using weakly-co-ordinating anions such as $BF_4^-$.

The diazonium salts are then reacted with activated aromatic compounds such as phenols, thiophenols, mono-arylated or alkylated phenylphosphanes, mono-arylated or alkylated anilines, benzoic acid or benzoic acid ester derivatives or aromatic amines. In this connection, in the case of phenols the corresponding alkali phenolates are first of all prepared and the reaction is carried out in a weakly acidic to alkaline pH range, preferably in the pH range 14 to 6. The azo compound formed is then purified by conventional methods such as filtration or phase separation. A more complete purification is carried out by column chromatography or crystallization using suitable solvents.

So that the compounds according to the present invention of the general formula (I) can be used as catalysts for the polymerization, they may be reacted with co-catalysts. Suitable co-catalysts are selected from the group of aluminum compounds and/or boron compounds with electron-attracting radicals. Preferred are boron trifluoride, trispentafluorophenyl borane, trispentafluorophenyl-aluminium, N,N-dimethylanilinium-tetrakis-pentafluorophenyl borate, tri-n-butylammonium-tetrakis-pentafluorophenyl borate, N,N-dimethylanilinium-tetrakis-(3,5-bisperfluoro-methyl)phenyl borate, tri-n-butylammonium-tetrakis-(3,5-bisperfluoromethyl)phenyl borate, as well as tritylium-tetrakis-pentafluoro-phenyl borate. More preferred are N,N-dimethylanilinium-tetrakis-pentafluorophenyl borate, tritylium-tetrakis-pentafluorophenyl borate and trispentafluorophenyl borane.

If boron compounds or aluminum compounds are used as co-catalysts for the compounds according to the invention of the general formula (I), then they are employed in general in a molar ratio of 1:10 to 10:1 referred to $M^1$, preferably in a molar ratio of 1:2 to 5:1 and more preferably 1:1.5 to 1.5:1.

Another suitable class of co-catalysts are aluminoxanes.

The structure of the aluminoxanes is not accurately known. As described in DE-A 3 007 725, these are products that are obtained by careful partial hydrolysis of aluminum alkyls. These products do not occur in pure form but as mixtures of open-chain and cyclic structures of the type (V a) and (V b). These mixtures presumably exist in the form of a dynamic equilibrium.

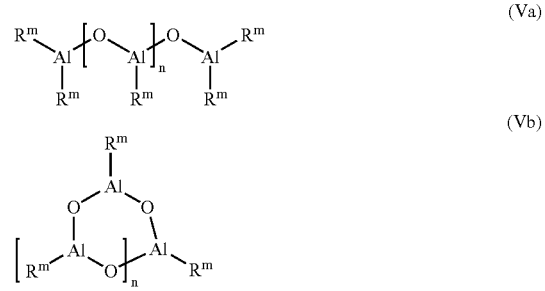

In formula (Va) and (Vb) the radicals $R^m$ are selected independently of one another from the group comprising substituted or unsubstituted $C_1$–$C_{12}$-alkyl groups, substituted or unsubstituted $C_3$–$C_{12}$-cycloalkyl groups, substituted or unsubstituted $C_7$–$C_{20}$-aralkyl groups, or substituted or unsubstituted $C_6$–$C_{14}$-aryl groups.

$C_1$–$C_{12}$-alkyl groups are understood to denote all alkyl groups with this number of carbon atoms in the main chain.

Preferred $C_1$–$C_{12}$-alkyl groups include methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, iso-heptyl, n-octyl, n-nonyl, n-decyl and n-dodecyl. More preferred are $C_1$–$C_6$-alkyl such as methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl. Most preferred is methyl.

$C_3$–$C_{12}$-cycloalkyl groups are understood to denote all cycloalkyl groups with this number of carbon atoms in the ring.

Preferred $C_3$–$C_{12}$-cycloalkyl includes cyclopropyl, cyclobutyl, cyclopentyl, cyclohexyl, cycloheptyl, cyclooctyl, cyclononyl, cyclodecyl, cycloundecyl and cyclododecyl. More preferred are cyclopentyl, cyclohexyl and cycloheptyl.

$C_7$–$C_{20}$-aralkyl groups are understood to denote all aralkyl groups with this number of carbon atoms in the main skeleton.

Preferred are $C_7$–$C_{20}$-aralkyl, more preferred are $C_7$–$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl. Most preferred is benzyl.

$C_6$–$C_{14}$-aryl groups are understood to denote all aryl groups with this number of carbon atoms in the ring. Preferred are $C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl. More preferred are phenyl, 1-naphthyl and 2-naphthyl. Most preferred is phenyl.

The parameter n in the formulae (V a) and (V b) denotes a whole number from 0 to 40, preferably from 1 to 25 and particularly preferably from 2 to 22.

In Organometallics 1996, 15, 2213–26 also cage-like structures for the aluminoxanes are discussed by Y. Koide, S. G. Bott, A. R. Barron. A. R. Barron also reports on such structures in Macromol. Symp. 1995, 97, 15–25. Both the cage-like structures as well as the structures of the formulae (V a) and (V b) are suitable as co-catalysts for the compounds according to the present invention of the general formula (I).

Mixtures of various aluminoxanes are preferred co-catalysts in those cases in which polymerization is carried out in a solution of a paraffin such as n-heptane or isododecane. A preferred mixture is CoMAO commercially obtainable from Witco GmbH and having the formula

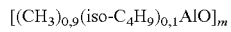

$[(CH_3)_{0.9}(iso\text{-}C_4H_9)_{0.1}AlO]_m$ where m is between 6 and 25.

In order to react the compounds according to the present invention of the general formula (I) with aluminoxanes, it is generally necessary to employ an excess of aluminoxane referred to $M^1$. Suitable molar ratios $M^1$:Al are in the range from 1:10 to 1:10,000, preferably 1:50 to 1:1000 and more preferably 1:100 to 1:500.

According to current ideas, co-catalysts for compounds of the general formula (I) remove a ligand $L^1$ or $L^2$. Instead of aluminum alkyl compounds of the general formulae (V a) and (V b) or the afore described aluminum compounds or boron compounds with electron-attracting radicals, the co-catalyst may also be olefin complexes of rhodium or nickel.

Preferred Ni-(olefin) complexes, which are commercially obtainable from Aldrich, have the following general structure: Nickel-(olefin)y complexes where y=1, 2, 3 or 4. More preferred are $Ni(C_2H_4)_3$, $Ni(1,5\text{-cyclooctadiene})_2$, $(Ni(COD)_2)$, $Ni(1,6\text{-cyclodecadiene})_2$, or $Ni(1,5,9\text{-all-trans-cyclododecatriene})_2$. Most preferred is $(Ni(COD)_2)$.

Suitable rhodium-(olefin) complexes are mixed ethylene/1,3-dicarbonyl complexes of rhodium such as rhodium-acetylacetonate-ethylene Rh (acac) $(CH_2=CH_2)_2$, rhodium-benzoylacetonate-ethylene Rh $(C_6H_5-CO-CH-CO-CH_3)$ $(CH_2=CH_2)_2$, or Rh $(C_6H_5-CO-CH-CO-C_6H_5)$ $(CH_2=CH_2)_2$. Preferred is Rh(acac) $(CH_2=CH_2)_2$. This compound can be synthesized by the procedure described by R. Cramer in Inorg. Synth. 1974, 15, 14.

With some compounds of the general formula (I) a reaction may also be carried out directly with ethylene. The ease of the starting reaction depends decisively on the nature of the ligand $L^1$. Such labile coordinating ligands $L^1$ are preferably compounds that possess an olefinic group and can thereby complex the metal. In addition particularly also nitrites and compounds with ether functions are suitable.

The selected compound of the general formula (I) and the co-catalyst together form a reaction product that is active as catalyst system in the polymerization.

By adding further aluminum alkyl of the general formula $Al(R^m)_3$ or aluminoxanes the activity of the catalyst system according to the invention can be increased, especially if compounds of the general formula (V a) and (V b) or the aforementioned aluminum compounds or boron compounds with electron-attracting radicals are used as co-catalysts; aluminum alkyls of the general formula $Al(R^m)_3$ or aluminoxanes may also act as molecular weight regulators. A further effective molecular weight regulator is hydrogen. The molecular weight can be particularly effectively regulated by the reaction temperature and pressure. In the case where the use of a boron compound as described above is desired, the addition of an aluminum alkyl of the general formula $Al(R^m)_3$ is preferred.

It has been found that the compounds according to the present invention of the general formula (I) are suitable for polymerizing olefins in the presence of polar additives such as esters, ethers and nitrites. They are effective for polymerizing and copolymerizing ethene.

Pressure and temperature conditions during the polymerization may be selected within wide ranges. A pressure in the range from 0.5 bar to 4000 bar has proved to be preferable, pressures of 10 to 75 bar or high pressure conditions of 500 to 2500 bar being more preferred. A temperature in the range from 0° to 120° C. has proved preferable, temperatures of 40° to 100° C. being more preferred and temperatures of 50° to 85° C. being most preferred.

As monomers the following olefins may be mentioned: ethylene, propylene, 1-butene, 1-pentene, 1-hexene, 1-octene, 1-decene or 1-undecene, propylene and ethylene being preferred and ethylene being more preferred.

As comonomers αolefins, styrene, isobutene, cyclopentene, cyclohexene, norbornene and norbornadiene are suitable. Preferred are 1-butene, 1-pentene, 1-hexene, 4-methyl-1-pentene, 1-octene, 1-decene or 1-undecene. The α-olefins are employed in amounts of 0.1 to 20 mole % referred to the polymer obtained. α-olefin amounts in the range from 0.5 to 10 mole % are preferred.

As solvents there are used hexane, heptane, toluene, ortho-xylene, meta-xylene, para-xylene, ethylbenzene as well as mixtures thereof, diethyl ether, tetrahydrofuran, chlorobenzene, 1,3-dichlorobenzene, dichloromethane and—under high pressure conditions—supercritical ethylene. Preferred are hexane, toluene, chlorobenzene and dichloromethane.

The compounds according to the present invention of the general formula (I) can be regulated with hydrogen during the polymerization, i.e. the molecular weight of the polymers obtained by the catalyst system can be reduced by addition of hydrogen. If a sufficiently large amount of hydrogen is added waxes are obtained, the necessary hydrogen concentration also depending on the nature of the polymerization equipment that is employed.

The catalysts according to the present invention may also be used jointly with one or more other polymerization catalysts known per se. They may be used together with:
  Ziegler-Natta catalysts,
  supported metallocene catalysts of transition metals of subgroups 4 to 6 of the Periodic System of the Elements,
  catalysts of late transition metals as described in WO 96/23010,
  Fe-complexes or Co-complexes with pyridyldiimine ligands, as disclosed in WO 98/27124,
  or also chromium oxide catalysts according to Phillips.

In this connection it is on the one hand possible to mix various catalysts with one another and to meter them jointly or to use co-supported complexes on a common support or also to meter various catalysts separately at the same or at different points in the polymerization vessel.

A further feature of the present invention is that the compounds according to the present invention of the general formula (I), preferably those where $M^1$=Ni, are suitable for the polymerization or co-polymerization of 1-olefins, preferably ethylene, in emulsion polymerization processes.

In addition to other 1-olefins as comonomers, such as propene, 1-butene, 1-hexene, 1-octene or 1-decene, polar comonomers can also be incorporated with the aid of the catalyst system, in which connection 0.1 to 50 mole % of comonomers may preferably be used. As polar comonomers, the following are preferred:
- acrylates such as acrylic acid, methyl acrylate, ethyl acrylate, (2-ethyl)hexyl acrylate, n-butyl acrylate or tert.-butyl acrylate;
- acrylonitrile
- methacrylic acid, methyl methacrylate, ethyl methacrylate, n-butyl methacrylate or tert.-butyl methacrylate,
- vinyl carboxylates, vinyl acetate being more preferred,
- unsaturated dicarboxylic acids, maleic acid being more preferred,
- unsaturated dicarboxylic acid derivatives, in which connection maleic anhydride and maleic acid alkylimides such as maleic acid methylimide are more preferred.

Furthermore terpolymers may be produced with at least two of the polar monomers mentioned above or a mixture of polar and non-polar monomers, in each case in a molecular range between 0.1 and 99.8 mole %, and ethylene.

The polymer produced with the aid of the compound according to the present invention can be processed into further molded articles by various methods known to the person skilled in the art, for example injection molding, extrusion or foaming.

EXAMPLES

The following operating examples illustrate the invention.

General Preliminary Remarks:

All operations were carried out using thin tubular equipment with the exclusion of air and moisture in a purified argon atmosphere. The apparatus were heated in an oil pump vacuum before use and flushed with purified argon. The NMR tubes were also filled under argon.

All solvents that were used for the reaction, including those that served for cleaning column chromatography apparatus, were free of water and atmospheric oxygen. Silica gel-coated (Polygram® SIL G/UV$_{254}$) or aluminum oxide gel-coated (Polygram® ALOX N/UV$_{254}$) thin-layer chromatography plates from Machery-Nagel were used for the thin-layer chromatographic investigation of the course of the reactions. The following sorbents were used for the column chromatography:
- Silica gel 60, grain size 40–60 μm, 230–400 mesh (ASTM) (Baker)
- Kieselguhr, purified, annealed, Erg. B. 6 (Reidel-de Haën).

NMR spectra were recorded in deuterated solvents at 293° K. The chemical shift is given in ppm (parts per million).

$^1$H-NMR: internal standard via solvent, CDCl$_3$ δ=7.26; C$_6$D$_6$δ=7.16; rel. SiMe$_4$ (where SiMe$_4$ δ=0).

$^{13}$C{$^1$H}-NMR: internal standard via solvent, CDCl$_3$δ=77.0; C$_6$D$_6$ =128.0; rel SiMe$_4$ (where SiMe$_3$ δ=0).

$^{31}$P{$^1$H}-NMR: external standard via 85% aqueous orthophosphoric acid.

Preparation of the ligands according to the present invention:

General Operational Procedure for the Diazotisation (Examples 1.1 to 1.4)

HBF$_4$ (mixture of 40 ml of 48% acid (64 mmole) and 40 ml of water) were slowly added to 2,4,6-trimethylaniline (72.4 mmole) while stirring at 0° C., a white suspension being formed. A solution of sodium nitrite in water (5.0 g, 71.4 mmole in 10 ml of water) wasadded dropwise thereto while stirring. The color of the reaction solution turned yellow. The suspension obtained was stirred for a firther 5 minutes and added in portions at 0° C. to a solution of the phenol in 2N NaOH (dissolve the phenol (71.4 mmole) in a small amount of ethanol and mix with 500 ml of a 2N NaOH solution). After 10 minutes a red oily layer was obtained that solidifiee after further stirring. After filtration the solid was crystallized from a small amount of ethanol and the Na salt of the azo dye was obtained.

The Na salt was dissolved in as small an amount of diethyl ether as possible and thoroughly mixed with dilute HCl. After separating the phases the organic phase was dried with Na$_2$SO$_4$ and finally, after filtration, all volatile constituents were removed in vacuo.

For the diazotisation with 2,6-diisopropylaniline the following typical procedure was adopted:

The ligands were obtained by a coupling reaction of the diazonium salt with the corresponding phenols. The diazonium salt was prepared by reaction of 2,6-diisopropylaniline (20 mmole) with isoamyl nitrite (2.9 g, 3.4 ml, 25 mmole) and BF$_3$*OEt$_2$ (3.1 g, 2.8 ml, 22 mmole) in methylene chloride (200 ml) at −10° C. within 60 minutes. After filtering off the diazonium salt (water jet vacuum) in the cold, the latter was suspended at −20° C. in TMF (50 ml) and added to a solution of phenol (20 mmole) (dissolved phenol in as small an amount of ethanol as possible and added NaOH (10 g, 250 rnmole) in 100 ml of water) at −20° C. (stir for 1 hour). The reaction solution was then heated to 25° C. while stirring vigorously and was stirred for a further 15 hours. The reaction solution was worked up by adding hexane, mixing thoroughly with dilute HCl, then washing with water to pH 7 and separating the aqueous phase. After drying the organic phase over Na$_2$SO$_4$ the was is chromatographed using silica gel with hexane/methylene chloride (3/1). A purified product was obtained by crystallization from methanol at −20° C.

Conversion of the Acid Azo Dyes Into the Corresponding Li Salts (Examples 2.1 to 2.4)

The azo dye (14.2 mmole) was dissolved in 150 ml of tetrahydrofuran and cooled to −78° C. Preferably diethyl ether may also be used if the azo dye was sufficiently soluble. n-BuLi (2.7 ml in heptane, 5.8 ml, 15.6 mmole) was then added dropwise and the reaction mixture was stirred at −78° C. for 1 hour. After heating to 25° C. the solvent was removed and 60 ml of n-hexane were added. The purified product was obtained by crystallization at −20° C. and may have been directly processed further.

Preparation of the Diazoenolate Ni Complexes (Examples 3.1 to 3.4)

The Li salt of the azo compound (3.0 mmole) was dissolved in 10 ml of benzene at 25° C. and a solution of (PPh$_3$)$_2$Ni(Ph)Cl in 20 ml of benzene was added thereto. The preparation of (PPh$_3$)$_2$Ni(Ph)Cl was carried out according to the procedure of Hidai, M., Kashiwagi, T., Ikeuchi, T., Uchida, Y. described in J. Organomet. Chem. 1971, 30, 279. The initially greenish-brown reaction mixture changed color to brownish-red after stirring for 15 hours. The solution was then filtered off from the precipitated LiCl and all volatile constituents were removed in vacuo. The residue was taken up in 10 ml of n-hexane and crystallized at −20° C.

Preparation of the Diazoenolate Pd Complexes (Examples 4.1 to 4.4)

The Li salt of the azo compound (1.5 mmole) was taken up in 10 ml of methylene chloride at 25° C. and the solution was cooled to 0° C. Parallel to this (COD)Pd(Me)Cl (1.5 mmole) was dissolved in 2 ml of $CH_2Cl_2$ and added to a concentrated solution of triphenylphosphine (3 mmole in 3 ml of $CH_2Cl_2$) at 0° C., a grey-white suspension being formed. The preparation of (COD)Pd(Me)Cl was carried out according to a procedure described by Rülke, R. E., Ernsting, J. M., Spek, A. L., Elsevier, C. J., van Leewen, P. W. M. N., Vrieze, K. in Inorg. Chem. 1993, 32, 5769.

This reaction mixture was added to the Li salt of the azo compound at 0° C. and stirred for 15 hours at 25° C. A red suspension was thus obtained. After removing all volatile constituents, 10 ml of toluene were added and insoluble constituents were filtered off. The solvent was then removed and the product was crystallized from 10 ml of hexane at −20° C.

The Li salt of the azo compound (1.5 mmole) was taken up in methylene chloride (10 ml) and pyridine (3.0 mmole) was added. (COD)Pd(Me)Cl (1.5 mmole) in methylene chloride (5 ml) was then added at 0° C. The reaction solution was stirred for 15 hours at 25° C. After removing all volatile constituents the product was dissolved in toluene and insoluble constituents were filtered off. The solvent was distilled off and hexane was added. Crystallization was carried out at −20° to −78° C.

TABLE 1

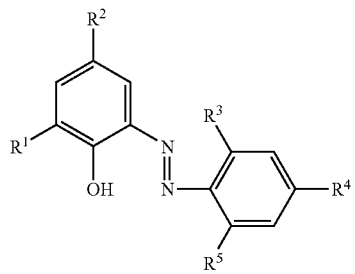

Azo compounds

| Example | $R^1$ | $R^2$ | $R^3$ | $R^4$ | $R^5$ |
|---------|-------|-------|-------|-------|-------|
| 1.1 | $^tBu$ | $^tBu$ | Me | Me | Me |
| 1.2 | $^tBu$ | $^tBu$ | $^iPr$ | H | $^iPr$ |
| 1.3 | Ph | $^tBu$ | Me | Me | Me |
| 1.4 | Ph | $^tBu$ | $^iPr$ | H | $^iPr$ |

TABLE 2

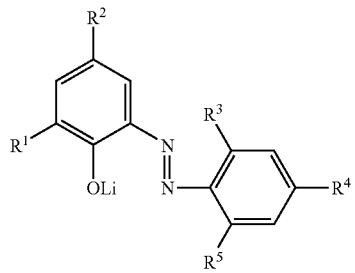

Lithium salts of the azo compounds

| Example | $R^1$ | $R^2$ | $R^3$ | $R^4$ | $R^5$ |
|---------|-------|-------|-------|-------|-------|
| 2.1 | $^tBu$ | $^tBu$ | Me | Me | Me |
| 2.2 | $^tBu$ | $^tBu$ | $^iPr$ | H | $^iPr$ |

TABLE 2-continued

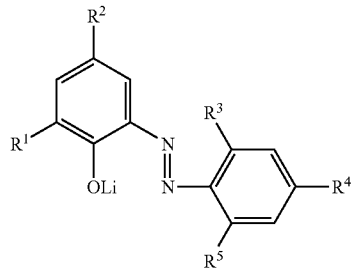

Lithium salts of the azo compounds

| Example | $R^1$ | $R^2$ | $R^3$ | $R^4$ | $R^5$ |
|---------|-------|-------|-------|-------|-------|
| 2.3 | Ph | $^tBu$ | Me | Me | Me |
| 2.4 | Ph | $^tBu$ | $^iPr$ | H | $^iPr$ |

TABLE 3

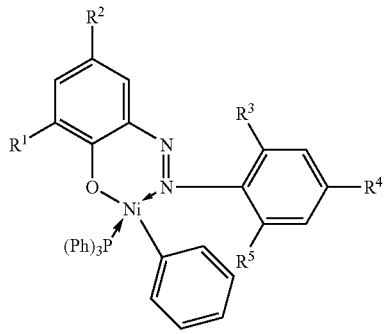

Nickel complexes

| Example | $R^1$ | $R^2$ | $R^3$ | $R^4$ | $R^5$ |
|---------|-------|-------|-------|-------|-------|
| 3.1 | $^tBu$ | $^tBu$ | Me | Me | Me |
| 3.2 | $^tBu$ | $^tBu$ | $^iPr$ | H | $^iPr$ |
| 3.3 | Ph | $^tBu$ | $^iPr$ | H | $^iPr$ |

TABLE 4

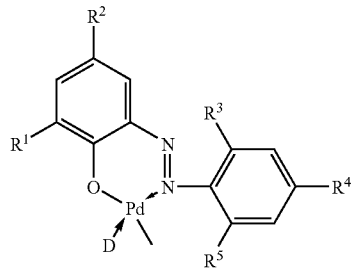

Palladium complexes

| Example | D | $R^1$ | $R^2$ | $R^3$ | $R^4$ | $R^5$ |
|---------|---|-------|-------|-------|-------|-------|
| 4.1 | P(Ph)$_3$ | $^tBu$ | $^tBu$ | Me | Me | Me |
| 4.2 | Py | $^tBu$ | $^tBu$ | Me | Me | Me |
| 4.3 | P(Ph)$_3$ | $^tBu$ | $^tBu$ | $^iPr$ | H | $^iPr$ |
| 4.4 | Py | Ph | $^tBu$ | $^iPr$ | H | $^iPr$ |

Analytical data relating to the compounds 1.1 to 1.4 and 3.1 to 4.2:

Azo Compounds:

Example 1.1

Anal. Calc. for $C_{23}H_{32}N_2O$ (352.51): C, 78.36; H, 9.15; N, 7.95; Found: C, 78.2; H, 9.1; N, 7.9. m.p.: 89° C. $^1$H-NMR in $CDCl_3$, [δ]: 1.30 (s, 9H, $CH_3$, t-Bu), 1.41 (s, 9H, $CH_3$, t-Bu), 2.26 (s, 3H, $CH_3$), 2.35 (s, 6H, $CH_3$), 6.89 (s, 2H, CH, Ar), 7.37 (d, 1H, $^4J_{HH}$=2.4 Hz, CH, Ar), 7.69 (d, 1H, $^4J_{HH}$=2.4 Hz, CH, Ar), 13.5 (1H, OH). $^{13}C\{^1H\}$-NMR in $CDCl_3$, [δ]: 19.7 ($CH_3$), 21.1 ($CH_3$), 29.5 ($CH_3$, t-Bu), 31.3 ($CH_3$, t-Bu), 34.3 (C, t-Bu), 35.3 (C, t-Bu). 127.2 (CH, Ar), 127.9 (CH, Ar), 130.3 (CH, Ar), 131.6 (CH, Ar), 137.0 (C, Ar), 137.9 (C, Ar), 138.7 (C, Ar), 141.2 (C, Ar), 146.3 (C, Ar), 149.9 (C, Ar). IR: 1360 (m, $δ_{(N=N)}$), (no OH).

Example 1.2

Anal. Calc. for $C_{26}H_{38}N_2O$ (394.59): C, 79.14; H, 9.71; N, 7.10; Found: C, 79.0; H, 10.4; N, 6.9. m.p.: 82° C. $^1$H-NMR in $CDCl_3$, [δ]: 1.20 (d, 12H, $^3J_{HH}$=7.8 Hz, $CH_3$; i-Pr), 1.37 (s, 9H, $CH_3$, t-Bu), 1.49 (s, 9H, $CH_3$, t-Bu), 3.05 (sp, 2H, $^3J_{HH}$=7.8 Hz, CH; i-Pr); 7.25–7.32 (m, 3H, CH, Ar), 7.50 (s, 1H, CH, Ar), 7.80 (s, 1H, CH, Ar), 13.2 (1H, OH). $^{13}C\{^1H\}$-NMR in $CDCl_3$, [δ]: 23.7 ($CH_3$, i-Pr), 27.9 (CH, i-Pr), 29.5 ($CH_3$, t-Bu), 31.4 ($CH_3$, t-Bu), 34.3 (C, t-Bu), 35.4 (C, t-Bu), 123.7 (CH, Ar), 127.7 (CH, Ar), 128.2 (CH, Ar), 128.6 (CH, Ar), 136.9 (C, Ar), 137.9 (C, Ar), 140.2 (C, Ar), 141.3 (C, Ar), 148.5 (C, Ar), 149.8 (C, Ar).

Example 1.3

Anal. Calc. for $C_{25}H_{28}N_2O$ (372.50) C, 80.61; H, 7.58; N, 7.52; Found: C, 78.9; H, 7.7; N, 7.2. m.p.: 111° C. $^1$H-NMR in $CDCl_3$, [δ]: 1.34 (s, 9H, $CH_3$, t-Bu), 2.26 (s, 3H, $CH_3$), 2.36 (s, 6H, $CH_3$), 6.90 (s, 2H, CH, Ar), 7.29 (t, 1H, CH, Ar), 7.39 (t, 2H, CH, Ar), 7.41 (s, 1H, CH, Ar), 7.57 (d, 2H, CH, Ar), 7.86 (s, 1H, CH, Ar), 13.3 (1H, OH). $^{13}C\{^1H\}$-NMR in $CDCl_3$, [δ]: 19.8 ($CH_3$), 21.1 ($CH_3$), 31.4 ($CH_3$, t-BU), 34.2 (C, t-Bu), 127.3 (CH, Ar), 128.2 (CH, Ar), 128.9 (CH, Ar), 129.5 (CH, Ar), 130.4 (CH, Ar), 131.7 (CH, Ar), 131.9 (CH, Ar), 137.2 (C, Ar), 137.8 (C, Ar), 139.2 (C, Ar), 142.4 (C, Ar), 146.2 (C, Ar), 147.5 (C, Ar). IR: 1373 (m, $δ_{(N=N)}$), (no OH).

Example 1.4

Anal. Calc. for $C_{28}H_{34}N_2O$ (414.58): C, 81.12; H, 8.27; N, 6.76; Found: C, 80.8; H, 8.4; N, 6.7. m.p.: 106° C. $^1$H-NMR in $CDCl_3$, [δ]: 1.20 (d, 12H, $^3J_{HH}$=6.9 Hz, $CH_3$; i-Pr), 1.42 (s, 9H, $CH_3$, t-Bu), 3.07 (sp, 2H, $^3J_{HH}$=6.9 Hz, CH; i-Pr); 7.28 (d, 2H, CH, Ar), 7.32 (t, 1H, CH, Ar), 7.39 (t, 1H, CH, Ar), 7.48 (t, 2H, CH, Ar), 7.55 (s, 1H, CH, Ar), 7.66 (d, 2H, CH, Ar), 7.98 (s, 1H, CH, Ar), 13.0 (1H, OH). $^{13}C\{^1H\}$-NMR in $CDCl_3$, [δ]: 23.7 ($CH_3$, i-Pr), 27.9 (CH, i-Pr), 31.4 ($CH_3$, t-Bu), 34.2 (C, t-Bu), 123.7 (CH, Ar), 127.4 (CH, Ar), 128.3 (CH, Ar), 128.4 (CH, Ar), 129.3 (CH, Ar), 129.5 (CH, Ar), 130.5 (CH, Ar), 132.4 (CH, Ar), 136.9 (C, Ar), 137.5 (C, Ar), 140.2 (C, Ar), 142.6 (C, Ar), 147.5 (C, Ar), 148.5 (C, Ar). IR: 1362 (m, $δ_{(N=N)}$), (no OH).

Nickel Complexes:

Example 3.1

Anal. Calc. for $C_{47}H_{51}N_2NiOP$ (749.59) C, 75.31; H, 6.86; N, 3.74; Ni, 7.83; O, 2.13; P, 4.13 Found: C, 75.5; H, 6.8; N, 2.7; P, 3.6. m.p.: 116° C. $^1$H-NMR in $CDCl_3$, [δ]: 0.58 (s, 9H, $CH_3$, t-Bu), 0.70 (s, 9H, $CH_3$, t-Bu), 1.99 (s, 3H, $CH_3$), 2.27 (s, 6H, $CH_3$), 5.95 (t, 2H, CH, Ar), 6.13 (t, 1H, CH, Ar), 6.41 (s, 2H, CH, Ar), 6.64 (d, 2H, CH, Ar), 7.1–7.7 (m, 22H, CH, Ar). $^{13}C\{^1H\}$-NMR in $CDCl_3$, [δ]: 19.2 ($CH_3$), 21.0 ($CH_3$), 29.9 ($CH_3$, t-Bu), 31.6 ($CH_3$, t-Bu), 34.4 (C, t-Bu), 35.3 (C, t-Bu), 121.4 (CH, Ar), 124.8 (CH, Ar), 127.2 (CH, Ar), 128.3 (CH, Ar), 128.4 (CH, Ar), 128.9 (CH, Ar), 129.6 (CH, Ar), 130.2 (CH, Ar), 131.8 (CH, Ar), 132.3 (CH, Ar), 132.5 (CH, Ar), 134.3 (C, Ar), 133.5 (C, Ar), 135.1 (CH, Ar), 136.8 (C, Ar), 137.3 (CH, Ar), 140.5 (C, Ar), 142.6 (C, Ar), 146.0 (C, Ar), 146.6 (C, Ar), 151.9 (C, Ar), 152.5 (C, Ar). $^{31}$P-NMR in $C_6D_6$, [δ]: 26.1 ($PPh_3$). MS (FD)[%]: 748 [54, M$^+$], 278 [76], 262 [100].

Example 3.2

$^1$H-NMR in $C_6D_6$, [δ]: 1.09 (s, 9H, $CH_3$, t-Bu), 1.35 (d, 6H, $^3J_{HH}$=6.7 Hz, $CH_3$, i-Pr), 1.43 (s, 9H, $CH_3$, t-Bu), 4.50 (sp, 2H, $^3J_{HH}$=6.7 Hz, CH, i-Pr), 6.38 (t, 2H, CH, Ar), 6.45 (t, 1H, CH, Ar), 7.3 (m, CH, Ar), 7.7–8.0 (m, CH, Ar). $^{13}C\{^1H\}$-NMR in $C_6D_6$, [δ]: 24.9 ($CH_3$, i-Pr), 27.9 ($CH_3$, i-Pr), 31.9 (CH, i-Pr), 32.4 ($CH_3$, t, Bu), 33.6 ($CH_3$, t-Bu), 36.3 (C, t-Bu), 37.6 (C, t-Bu), 123.5 (CH, Ar), 125.9 (CH, Ar), 129.3 (CH, Ar), 130.0 (CH, Ar), 131.9 (CH, Ar), 132.4 (CH, Ar), 132.5 (CH, Ar), 134.7 (CH, Ar), 134.8 (CH, Ar), 137.3 (CH, Ar), 137.3 (CH, Ar), 139.5 (C, Ar), 140.5 (C, Ar), 142.8 (C, Ar), 143.5 (C, Ar), 145.0 (C, Ar), 149.5 (C, Ar), 149.0 (C, Ar), 154.4 (C, Ar). $^{31}$P-NMR in $C_6D_6$, [δ]: 25.1 ($PPh_3$). MS (FD)[%]: 790 [100, M$^+$].

Example 3.3

$^1$H-NMR in $CDCl_3$, [δ]: 1.32 (d, 6H, $^3J_{HH}$=6.7 Hz, $CH_3$, i-Pr), 1.34 (s, 9H, $CH_3$, t-Bu), 4.18 (sp, 2H, $^3J_{HH}$=6.7 Hz, CH, i-Pr), 6.35 (t, 2H, CH, Ar), 6.44 (t, 1H, CH, Ar), 6.83 (t, 2H, CH, Ar), 6.87 (t, 1H, CH, Ar), 6.9–7.2 (m, 15H, CH, Ar), 7.47 (t, 4 H, J=5.7 Hz, CH, Ar), 7.57 (t, 4H, J=9.0 Hz, CH, Ar), 7.69 (d, 1H, J=2.8 Hz, CH, Ar), 7.83 (dd, 2H, CH, Ar), 8.05 (d, 1H, J=5.7 Hz, CH, Ar), $^{13}C\{^1H\}$-NMR in $C_6D_6$, [δ]: 22.5 ($CH_3$, i-Pr), 25.5 ($CH_3$, i-Pr), 29.4 (CH, i-Pr), 31.2 ($CH_3$, t-Bu), 34.9 (C, t-Bu), 121.6 (CH, Ar), 122.7 (CH, Ar), 125.5 (CH, Ar), 125.9 (CH, Ar), 127.0 (CH, Ar), 127.6 (CH, Ar), 127.9 (CH, Ar), 128.4 (CH, Ar), 128.5 (CH, Ar), 128.6 (CH, Ar), 129.2 (CH, Ar), 129.8 (CH, Ar), 129.9 (CH, Ar), 131.2 (C, Ar), 131.6 (C, Ar), 134.0 (C, Ar), 134.4 (CH, Ar), 134.5 (CH, Ar), 135.4 (C, Ar), 137.1 (C, Ar), 138.5 (C, Ar), 140.2 (C, Ar), 140.4 (C, Ar), 146.0 (C, Ar), 146.4 (C, Ar), 146.8 (C, Ar), 150.1 (C, Ar), 151.9 (C, Ar). $^{31}$P-NMR in $C_6D_6$, [δ]: 21.9 ($PPh_3$). MS (FD)[%]: 810 [100, M$^+$], 545 [12], 278 [36].

Palladium Complexes:

Example 4.1

Anal. Calc. for $C_{42}H_{49}N_2OPPd$ (735.25) C, 68.61; H, 6.72; N, 3.81; O, 2.18; P, 4.21; Pd, 14.47 Found: C, 68.4; H, 6.8; N, 3.6, Decomp.: 180° C. $^1$H-NMR in i $CDCl_3$, [δ]: −0.29 (d, 3H, $^3J_{P,H}$=4.2 Hz, $CH_3$), 0.79 (s, 9H, $CH_3$, t-Bu), 1.29 (s, 9H, CH$_3$, t-Bu), 2.18 (s, 3H, CH$_3$), 2.30 (s, 6H, CH$_3$), 6.90 (s, 2H, CH, Ar), 7.32–7.45 (m, CH, Ar), 7.47 (s, 1H, CH, Ar) 7.65–7.75 (m, CH, Ar). $^{13}$C{$^1$H}-NMR in CDCl$_3$, [δ]: 0.3 (CH$_3$), 18.4 (CH$_3$), 20.9 (CH$_3$), 29.3 (CH$_3$, t-Bu), 31.1 (CH$_3$, t-Bu), 33.8 (C, t-Bu), 35.1 (C, t-Bu), 128.1 (CH, Ar), 128.2 (CH, Ar), 128.7 (CH, Ar), 130.1 (CH, Ar), 130.2 (CH, Ar), 131.3 (C, Ar), 131.6 (C, Ar), 134.9 (CH, Ar), 135.0 (CH, Ar), 135.6 (C, Ar), 139.0 (C, Ar), 142.2 (C, Ar), 150.0 (C, Ar), 150.1 (C, Ar), 155.7 (C, Ar). $^{31}$P-NMR in CDC$_6$, [δ]: 35.5 (PPh$_3$). MS (FD)[%]: 734 [100, M$^+$].

Example 4.2

Anal. Calc. for C$_{29}$H$_{39}$N$_3$OPd (552.06) C, 63.09; H, 7.12; N, 7.61; O, 2.90; Pd, 19.28; Found: C, 62.5; H, 7.0; N, 7.6. Decomp.: 170° C. $^1$H-NMR in CDCl$_3$, [δ]: −0.05 (s, 3H, CH$_3$), 1.23 (s, 9H, CH$_3$, t-Bu), 1.24 (s, 9H, CH$_3$, t-Bu), 2.23 (s, 6H, (CH$_3$), 2.27 (s, 3H, CH$_3$), 6.89 (s, 2H, CH, Ar), 7.35 (t, 2H, CH, Py), 7.41 (s, 1H, CH, Ar), 7.45 (s, 1H, CH, Ar), 7.80 (t, 1H, CH, Py), 8.87 (d, 2H, CH, Py). $^{13}$C{$^1$H}-NMR in CDCl$_3$, [δ]: −3.9 (CH$_3$), 17.0 (CH$_3$), 19.9 (CH$_3$), 28.3 (CH$_3$, t-Bu), 2.84 (CH$_3$, t-Bu), 32.9 (C, t-Bu), 34.6 (C, t-Bu), 123.4 (CH, Py), 127.6 (CH, Ar), 128.4 (CH, Ar), 128.8 (CH, Py), 129.4 (CH, Ar), 133.9 (C, Ar), 134.6 (C, Ar), 136.3 (CH, Py), 136.4 (C, Ar), 138.4 (C, Ar), 140.1 (C, Ar), 149.7 (C, Ar), 151.5 (CH, Py), 154.6 (C, Ar). MS (FD)[%]: 551 [100, M$^+$].

Example 4.3

Anal. Calc. for C$_{45}$H$_{55}$N$_2$OPPd (777.32) C, 69.53; H, 7.13; N, 3.60; O, 2.06; P, 3.98; Pd, 13.69 Found: C, 70.6; H, 7.5; N, 3.3; m.p.: 199° C. $^1$H-NMR in CDCl$_3$, [δ]: −0.26 (d, 3H, $^3J_{PH}$=4.3 Hz, CH$_3$), 0.74 (s, 9H, CH$_3$, t-Bu), 1.20 (d, 6H, $^3J_{HH}$=6.8 Hz, CH$_3$, i-Pr), 1.30 (s, 9H, CH$_3$, t-Bu), 1.32 (d, 6H, $^3J_{HH}$=6.8 Hz, CH$_3$, i-Pr), 3.47 (sp, 2H, $^3J_{HH}$=6.8 Hz, CH, i-Pr), 7.20 (s, 1H, CH), 7.21 (s, 2H, CH), 7.38 (t, 6 H, CH), 7.42 (dt, 3H, CH), 7.46 (s, 1H, CH, Ar), 7.68 (dd, 6H, CH). $^{13}$C{$^1$H}-NMR in CDCl$_3$, [δ]: 2.5 (CH$_3$), 22.8 (CH$_3$, i-Pr), 24.6 (CH$_3$, i-Pr), 27.9 (CH, i-Pr), 29.3 (CH$_3$, t-Bu), 31.1 (CH$_3$, t-Bu), 33.8 (C, t-Bu), 35.1 (C, t-Bu), 123.2 (CH, Ar), 126.9 (CH, Ar), 128.2 (CH, Ar), 129.0 (CH, Ar), 130.3 (CH, Ar), 131.3 (C), 131.5 (C), 134.8 (CH, Ar), 134.9 (CH, Ar), 138.7 (C), 140.8 (C), 142.3 (C), 150.2 (C), 155.6 (C). $^{31}$P-NMR in CDCl$_6$, [δ]: 35.8 (PPh$_3$). MS (FD)[%]: 776 [100, M$^+$], 394 [56, M-PdMeP(Ph)$_3$].

Example 4.4

Anal. Calc. for C$_{34}$H$_{41}$N$_3$OPd(614.13) C, 66.49; H, 6.73; N, 6.84; O, 2.61; Pd, 17.33, Found: C, 65.7; H, 6.6; N, 6.8. Decomp: 175° C. $^1$H-NMR in CDCl$_3$, [δ]: −0.0 (s, 3H, CH$_3$), 1.04 (d, 6H, $^3J_{HH}$=6.8 Hz, CH$_3$, i-Pr), 1.24 (s, 9H, CH$_3$, t-Bu), 1.25 (d, 6H, $^3J_{HH}$=6.8 Hz, CH$_3$, i-Pr), 3.39 (sp, 2H, $^3J_{HH}$=6.8 Hz, CH, i-Pr), 7.1–7.3 (m, 8H, CH), 7.49 (s, 2H, CH), 7.50 (s, 1H, CH, Ar), 7.53 (s, 1H, CH, Ar), 7.66 (t, 1H, CH, Py), 8.53 (d, 2H, CH, Py). $^{13}$C{$^1$H}-NMR in CDCl$_3$, [δ]: 0.0 (CH$_3$), 22.6 (CH$_3$, i-Pr), 24.5 (CH$_3$, i-Pr), 27.7 (CH, i-Pr), 31.1 (CH$_3$, t-Bu), 33.7 (C, t-Bu), 123.2 (CH, Ar), 124.1 (CH, Ar), 126.2 (CH, Ar), 127.2 (CH, Ar), 127.4 (CH, Ar), 129.8 (CH, Ar), 130.9 (CH, Ar), 134.0 (C), 134.5 (CH, Ar), 136.5 (C), 137.5 (CH, Py), 139.2 (C), 140.1 (C), 150.7 (C), 152.2 (CH, Py), 153.8 (C). MS (FD)[%]: 613 [100, M$^+$].

Polymerization Examples:

General Operational Procedure for the Polymerization

Toluene, the co-catalyst and the azo complex were added in this order through a cannula to a sealable 300 ml steel autoclave provided with a glass insert. The mixture was then stirred for 30 minutes at 30° C. and ethene was then introduced to a pressure of 8 bar. The polymerization time was 2 hours and the temperature of the exothermic reaction was not controlled. After completion of the reaction the pressure of the reactor was released and the polymerization was stopped by adding a mixture of 5 ml of isopropanol and 5 ml of methanol. The contents of the autoclave were then poured into 300 ml of methylene/HCl and the precipitated polymer was dried after filtration.

TABLE 5

Examples of the polymerization of ethene without polar additives.

| Ex. No. | Total Volume (ml) | Catalyst | Catalyst (mmole) | Co-Catalyst | Co-Catalyst (mmole) | Additive | Additive (mmole) | Temp. (° C.) | Time (h) | Ethene (bar) | Yield (g) |
|---|---|---|---|---|---|---|---|---|---|---|---|
| 5.1 | 40 | 3.1 | 0.043 | B(C$_6$F$_5$)$_3$/diethyl ether (1:1) | 0.129 | — | — | 30 | 2 | 8 | 0.89 |
| 5.2 | 42 | 3.2 | 0.043 | B(C$_6$F$_5$)$_3$/diethyl ether (1:1) | 0.129 | — | — | 50 | 2 | 8 | 1.9 |
| 5.3 | 42 | 3.2 | 0.043 | B(C$_6$F$_5$)$_3$ | 0.129 | — | — | 30/60 | 1 each | 8 | 1.9 |
| 5.4 | 42 | 3.2 | 0.043 | BF$_3$/diethyl ether (1:1) | 0.129 | — | — | 30 | 2 | 8 | C$_4$–C$_8$-oligomers |

TABLE 6

Examples of the polymerization of ethene with polar additives.

| Ex. No. | Total Volume (ml) | Catalyst | Catalyst (mmole) | Co-Catalyst | Co-Catalyst (mmole) | Additive | Additive (mmole) | Temp. (° C.) | Time (h) | Ethene (bar) | Yield (g) |
|---|---|---|---|---|---|---|---|---|---|---|---|
| 6.1 | 43 | 3.2 | 0.043 | B(C$_6$F$_5$)$_3$/diethyl ether (1:1) | 0.129 | Diethyl ether | 0.43 | 30 | 2 | 8 | 1.01 |
| 6.2 | 43 | 3.2 | 0.043 | B(C$_6$F$_5$)$_3$/diethyl ether (1:1) | 0.129 | Diethyl ether | 4.3 | 30 | 2 | 8 | 2.3 |

TABLE 6-continued

Examples of the polymerization of ethene with polar additives.

| Ex. No. | Total Volume (ml) | Catalyst | Catalyst (mmole) | Co-Catalyst | Co-Catalyst (mmole) | Additive | Additive (mmole) | Temp. (° C.) | Time (h) | Ethene (bar) | Yield (g) |
|---|---|---|---|---|---|---|---|---|---|---|---|
| 6.3 | 43 | 3.2 | 0.043 | B(C$_6$F$_5$)$_3$/diethyl ether (1:1) | 0.129 | Diethyl ether | 43 | 30 | 2 | 8 | 1.93 |
| 6.4 | 43 | 3.2 | 0.043 | B(C$_6$F$_5$)$_3$/diethyl ether (1:1) | 0.129 | Ethyl acetate in each case | 0.43 | 30 | 2 | 8 | 1.73 |
| 6.5 | 43 | 3.2 | 0.043 | B(C$_6$F$_5$)$_3$/diethyl ether (1:1) | 0.129 | Ethyl acetate in each case | 4.3 | 30 | 2 | 8 | 1.73 |
| 6.6 | 43 | 3.2 | 0.043 | B(C$_6$F$_5$)$_3$/diethyl ether (1:1) | 0.129 | Ethyl acetate in each case | 43 | 30 | 2 | 8 | 1.01 |

Polymerization Examples for Catalysts Produced In Situ:

Nickel [Ni] Catalyst Mixture

The Li salt of the azo compound was dissolved in 1 ml of toluene. 1 ml of chlorobenzene was added to this solution. Ni(COD)$_2$ dissolved in 1 ml of toluene was then added at −20° C. The resultant solution was heated to 25° C. and then used for the polymerization.

Palladium [Pd] Catalyst Mixture

The azo compound was dissolved in 3 ml of toluene and added at 0° C. to a suspension of the palladium complex in 3 ml of 1,5-cyclooctadiene. The reaction solution was stirred for 2 hours at 25° C.

General Operating Procedure for the Polymerization

Toluene, the polar additive, the activator and solution of the catalyst mixture were added in this order through a cannula to a sealable 300 ml steel autoclave provided with a glass insert. The mixture was then stirred for 30 minutes at 30° C. and ethene was then introduced to a pressure of 8 bar. The duration of the polymerization was 2 hours and the temperature of the exothermic reaction was not controlled. After completion of the reaction the pressure of the reactor was released and the polymerization was stopped by adding a mixture of 5 ml of isopropanol and 5 ml of methanol. The contents of the autoclave were then poured into 300 ml of methylene/HCl and the precipitated polymer was dried after filtration.

TABLE 7

Examples of the polymerization of ethene without polar additives.

| Ex. No. | Total Volume (ml) | Ligand | Ligand (mmole) | Activator | Activator (mmole) | Metal Component [M] (mmole) | Additive | Additive (mmole) | Temp. (° C.) | Time (h) | Ethene (bar) | Yield (g) |
|---|---|---|---|---|---|---|---|---|---|---|---|---|
| 7.1 | 43 | 2.1 | 0.129 | B(C$_6$F$_5$)$_3$/diethyl ether (1:1) | 0.129 | [Ni] (0.129) | — | — | 30/60 | 1 each | 8 | 0.99 |
| 7.2 | 43 | 2.2 | 0.129 | B(C$_6$F$_5$)$_3$/diethyl ether (1:1) | 0.129 | [Ni] (0.129) | — | — | 30/60 | 1 each | 8 | 1.80 |

[Ni]: Ni(COD)$_2$, toluene

TABLE 8

Examples of the polymerization of ethene with polar additives.

| Ex. No. | Total Vol. (ml) | Ligand | Ligand (mmole) | Activator | Activator (mmole) | Metal Component [M] (mmole) | Additive | Additive (mmole) | Temp. (° C.) | Time (h) | Ethene (bar) | Yield (g) |
|---|---|---|---|---|---|---|---|---|---|---|---|---|
| 8.1 | 43 | 2.2 | 0.043 | B(C$_6$F$_5$)$_3$/diethyl ether (1:1) | 0.129 | [Ni] (0.043) | Diethyl ether | 4.3 | 30/60 | 1 each | 8 | 2.95 |
| 8.2 | 43 | 2.2 | 0.043 | B(C$_6$F$_5$)$_3$/diethyl ether (1:1) | 0.129 | [Ni] (0.043) | Methyl acetate | 4.3 | 30/60 | 1 each | 8 | 0.7 |
| 8.3 | 43 | 2.2 | 0.043 | B(C$_6$F$_5$)$_3$/diethyl ether (1:1) | 0.129 | [Ni] (0.043) | Acetonitrile | 4.3 | 30/60 | 1 each | 8 | 1.0 |
| 8.4 | 43 | 2.2 | 0.043 | B(C$_6$F$_5$)$_3$/diethyl ether (1:1) | 0.129 | [Ni] (0.043) | Acrylonitrile | 4.3 | 30/60 | 1 each | 8 | 0 (oligomer) |

[Ni]: Ni(COD)$_2$, toluene

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound according to formula 1

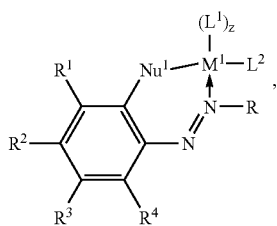

(I)

wherein $Nu^1$ is O,

R is mesityl, 2,4,6-trimethylphenyl or 2,6-diisopropylphenyl, $R^1$, $R^2$, $R^3$ and $R^4$ are identical or different radicals and independently of one another are selected from the group consisting of H, $C_1$–$C_8$-alkyl groups and $C_6$–$C_{14}$-aryl groups, $M^1$ is selected from the group consisting of Ti, Zr, Cr, V, Fe, Co, Ni, Pd, Cu and Zn $L^1$ is a neutral ligand selected from the group consisting of triphenylphosphine, triethylphosphine, trimethylphosphine, dibenzo-phosphol, triphenyl phosphite, triethyl phosphite, trimethyl phosphite, triphenyl phosphite, trimethyl-amine, triethylamine, dimethylaniline, diethylaniline, benzyl-dimethylamine, benzyl-diethylamine, diisopropylamine, diethylamine, dimethylamine, diphenylamine, phenylenediamines, diethyl ether, tetrahydrofuran, water, methanol, ethanol, pyridine, 2-picoline 3-picoline, 4-picoline, 2,3-lutidine, 2,4-lutidine, 2,5-lutidine, 2,6-lutidine, 3,5-lutidine, CO, acrylonitrile, acetonitrile, propionitrile, butyronitrile, benzonitrile, ethenyl, propenyl, cis-2-butenyl, trans-2-butenyl, cyclohexenyl and norbornenyl, $L^2$ is an anionic ligand selected from the group consisting of chloride, bromide, dimethylamide, diethylamide, amide, 2-carboxylic acid methallyl ester, allyl, methyl, ethyl, n-propyl, i-propyl, n-butyl, tert.-butyl, hexyl and phenyl z may be a whole number from 1 to 3.

2. A compound according to formula 1

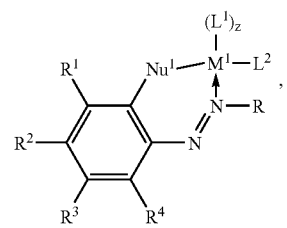

(I)

wherein $Nu^1$ is O,

R is mesityl or 2,6-diisopropylphenyl,

R is tert.-butyl or phenyl, $R^2$ is H, $R^3$ is tert.-butyl, $R^4$ is H, $M^1$ is Ni or Pd, $L^1$ is triphenylphosphane or pyridine, $L^2$ is phenyl or methyl and z is a whole number from 1 to 3.

* * * * *